United States Patent [19]

Chandler

[11] Patent Number: 4,660,026
[45] Date of Patent: Apr. 21, 1987

[54] FLUID STATE DETECTOR

[75] Inventor: Brian L. Chandler, Indianapolis, Ind.

[73] Assignee: Emhart Industries, Inc., Indianapolis, Ind.

[21] Appl. No.: 822,268

[22] Filed: Jan. 24, 1986

[51] Int. Cl.[4] .............................................. G08B 21/00
[52] U.S. Cl. ..................................... 340/604; 73/49.2;
73/46; 73/295; 338/22.R; 340/605; 340/620;
340/622
[58] Field of Search ............... 340/604, 605, 622, 620;
73/295, 204, 61.1, 46, 49.2; 338/22.R, 23, 24;
323/366, 369

[56] References Cited

U.S. PATENT DOCUMENTS

| | | | |
|---|---|---|---|
| 2,926,299 | 2/1960 | Rogoff | 73/204 |
| 2,947,938 | 8/1960 | Bennett | 73/204 X |
| 2,965,888 | 12/1960 | Johnston et al. | 340/622 X |
| 3,059,443 | 10/1962 | Garner | 340/622 X |
| 3,181,557 | 5/1965 | Lannan, Jr. | 73/295 X |
| 3,335,606 | 8/1967 | Scarpa | 338/23 X |
| 3,400,582 | 9/1968 | Warner | 73/204 X |
| 3,576,472 | 4/1971 | Marshall | 361/165 |
| 3,712,116 | 1/1973 | Andre | 73/53 |
| 3,757,317 | 9/1973 | Kahn et al. | 340/622 X |
| 4,116,045 | 9/1978 | Potter | 73/61.1 R |
| 4,135,396 | 1/1979 | Stanke et al. | 73/204 |
| 4,159,638 | 7/1979 | Potter | 73/61.1 R |
| 4,221,125 | 9/1980 | Oliver et al. | 73/61.1 R |
| 4,564,834 | 1/1986 | Steele | 340/622 |

Primary Examiner—James L. Rowland
Assistant Examiner—Daniel Myer
Attorney, Agent, or Firm—Robert F. Meyer; Carl A. Forest

[57] ABSTRACT

Two thermistors are mounted in a fluid detection probe, one thermistor having its surface exposed to the ambient fluids, and the other encapsulated in an insulator, such as RTV, that has a thermal conductivity greater than air. The thermistors are connected in a resistance bridge circuit between ground and a positive digital circuit voltage, which circuit applies power to the thermistors, heating them. The side of the thermistors toward the positive voltage is connected to the inputs of a comparator. When air is present, the encapsulated resistor cools more than the exposed one and, therefore, the encapsulated resistors resistance is higher producing a higher voltage at its comparator input than the exposed resistor. In the presence of a liquid, the RTV insulates its thermistor from the cooling effect of the liquid, and its comparator input voltage is therefore lower than the voltage of the exposed thermistor comparator input. Thus, the output of the comparator switches upon the environment of the thermistors changing from liquid to air, and its output is indicative of the fluid state of the probe environment. There is also a polar-non-polar liquid detector. The outputs of the comparator and the polar-non-polar detector are connected to a logic circuit, the output of which indicates the presence of air, water, or hydrocarbon.

7 Claims, 15 Drawing Figures

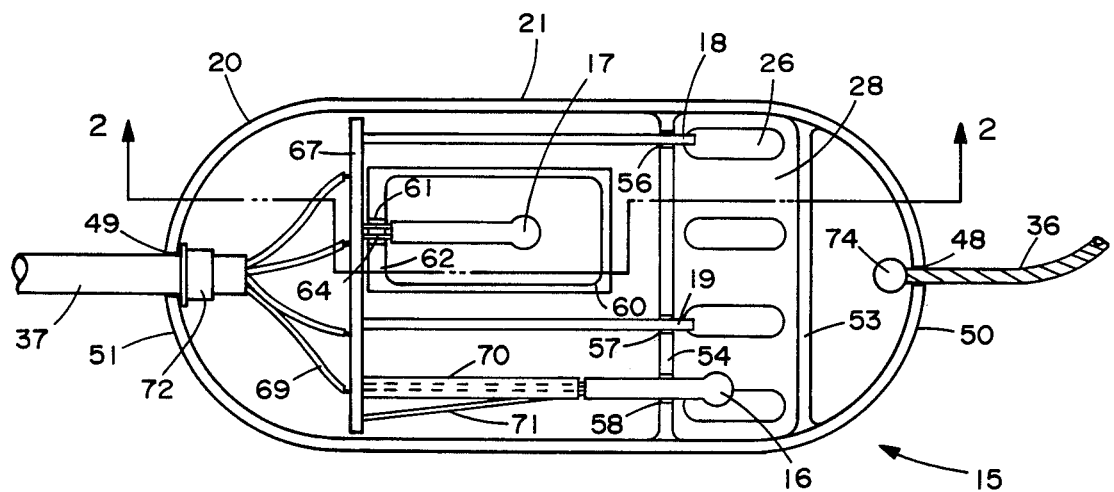
FIG. 1
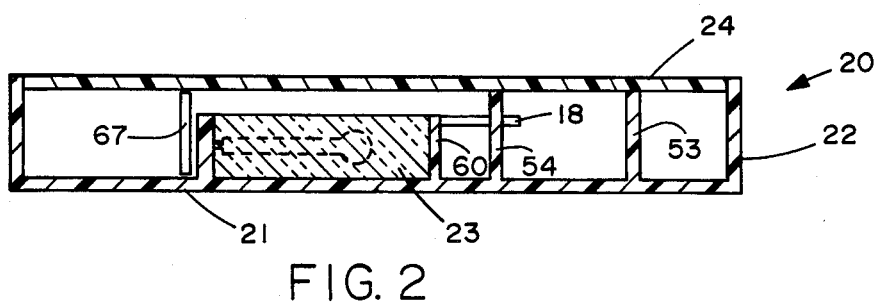
FIG. 2
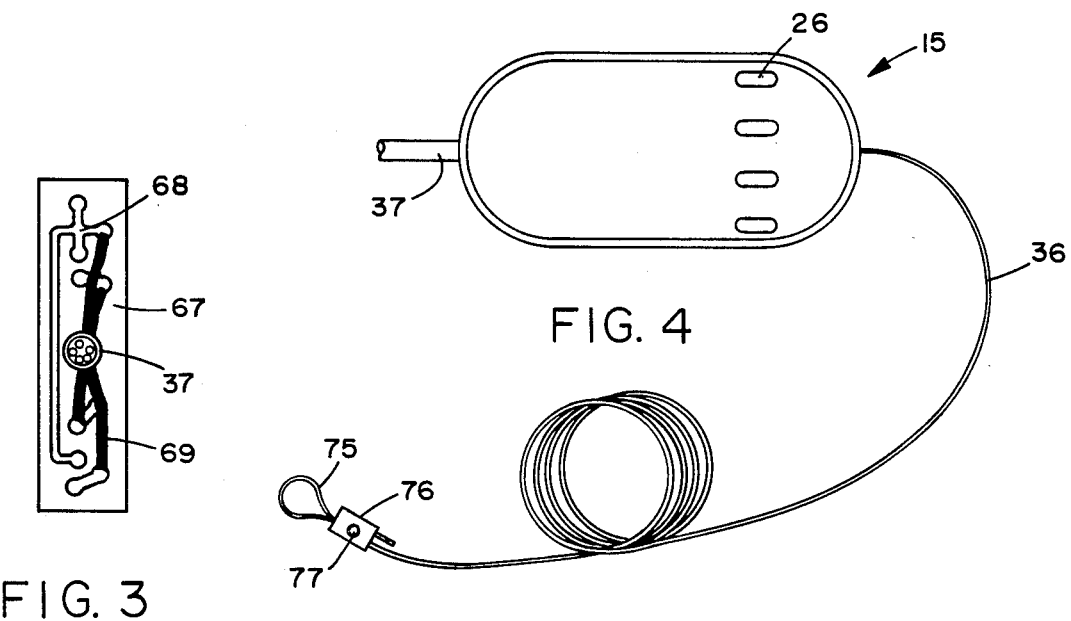
FIG. 3
FIG. 4

4,660,026

FLUID STATE DETECTOR

BACKGROUND OF THE INVENTION

1. Field of the Invention.

The invention in general relates to fluid detectors and in particular to fluid detectors that are used in combination with polar-non-polar liquid detectors to produce outputs indicative of the presence of air (or dry condition) water and hydrocarbon.

2. Description of the Prior Art.

Thermistors and other devices that have a temperature-dependent electrical property have long been used to differentiate between materials. See for example U.S. Pat. Nos. 3,576,472 issued to John F. Marshall, III, 3,712,116 issued to Marshall L. Andre, 4,116,045 issued to Bronson M. Potter, and 4,221,125 issued to John N. Oliver and Louis M. Sandler. Generally, two thermistors are used, one immersed in the material to be monitored and the other acting as a reference. (See the Marshall, Andre and Potter patents listed above.) Although the prior art two-thermistor-based detection systems work well in the laboratory or manufacturing situations where the environments of the thermistors can be closely controlled, in natural settings, such as the ground around gasoline storage tanks, problems arise in obtaining reliable differentiation between the two thermistors. Thus complicated probe systems and electronics have been developed to attempt to deal with this problem. See the Potter and Oliver et al patents referenced above. Even these complicated solutions have not been wholly reliable, and the hydrocarbon detection industry has generally replaced the thermistor-based systems with systems based on a combination of a float and conductivity sensor. See for example, U.S. Pat. No. 4,586,033. Although such systems generally work well, they have the disadvantages that the probes are relatively large and thus do not fit into small spaces, and the probes must be oriented essentially vertically for the floats to work properly.

SUMMARY OF THE INVENTION

It is an object of the invention to provide a fluid detector that is reliable in a natural, uncontrolled environment and at the same time is small enough to fit between the walls of a double-walled tank.

It is another object of the invention to provide a thermistor based fluid detector that has a simple probe system and simple electronics and is also highly reliable in a natural, uncontrolled environment.

It is a further object of the invention to provide a small detector that reliably differentiates between air (dry condition), water and hydrocarbon.

It is yet another object of the invention to provide a detector that provides one or more of the above objects and operates reliably in all orientations.

The invention provides apparatus for detecting the presence of fluids comprising a first monitoring element having a surface exposed for contact with the fluids to be monitored, a second monitoring element having a surface encapsulated in a thermal insulator, each of the monitoring elements having an electrical characteristic that changes with temperature, and electrical circuit means for heating the monitoring elements, the circuit including output means responsive to the electrical characteristic change to provide an indication of the fluid environment of the elements. Preferably, the thermal insulator is one that has a thermal conductivity greater than air, for example, RTV. Preferably, there are also third and fourth monitoring elements, a means for providing an oscillating voltage to the third and fourth monitoring elements and polar-non-polar fluid detector means for providing a fluid polar characteristic signal, and the output means includes a fluid state detector means for providing a fluid state characteristic signal, and logic means responsive to the fluid polar characteristic signal and the fluid state characteristic signal for providing an indication of whether the fluid is a gas or a polar or non-polar liquid.

The fluid state detector of the invention not only provides the objects and advantages described above, but it is relatively inexpensive to manufacture compared to the prior art devices. Numerous other features, objects and advantages will become apparent from the following detailed description when used in conjunction with the accompanying drawings.

BRIEF DESCRIPTION OF THE DRAWINGS

In the drawings

FIG. 1 is a plan view of a probe according to the invention without the encapsulating material and having the cover of the casing removed to show the fluid monitoring elements;

FIG. 2 is a cross-sectional view of a probe according to the invention taken through the line 2—2 of FIG. 1 including the encapsulating material and with the casing cover in place;

FIG. 3 is an end plan view of the connector for connecting the electrical cable to the monitoring elements;

FIG. 4 is an external view of the probe of FIG. 1 (with the cover in place) showing details of the probe lead;

DESCRIPTION OF THE PREFERRED EMBODIMENT

Figure 5A:
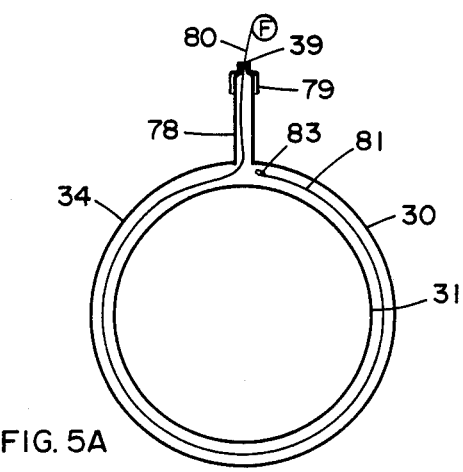
FIGS. 5A through 5D show the preferred method of installing a probe between the walls of a double-walled tank.
Figure 5B:
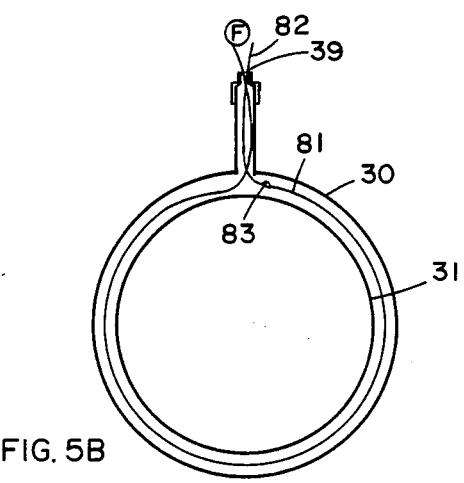
Figure 5C:
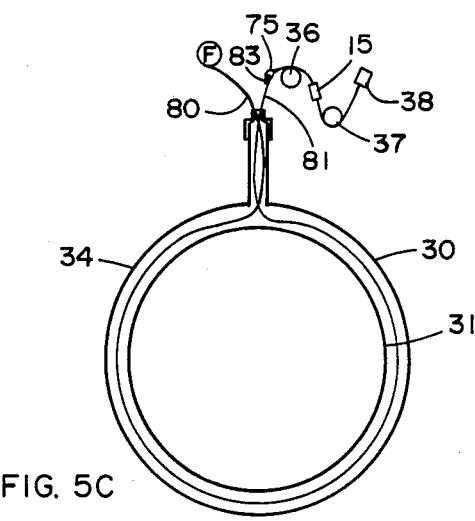

Directing attention to FIG. 1, a plan view of the interior of the preferred embodiment of a detector probe 15 according to the invention is shown. A first monitoring element 16, a second monitoring element 17, a third monitoring element 18, and a fourth monitoring element 19 are enclosed in a probe casing 20. The second monitoring element 17 is enclosed in a frame 60 which is shown empty in FIG. 1 to show the element. The frame 60 is filled with insulating material 23 to encapsulate the element (FIG. 2). The casing 20 is closed with a cover 24 (FIG. 2) and includes openings 26 to permit external fluid to enter a chamber 28 within the casing in which monitoring elements 16, 18, and 19 are exposed. The compact size and shape of the probe 15 permits it to be inserted into the space between the inner and outer walls 30 and 31 (FIGS. 5A through 5D) of a tank 34, such as an underground gasoline storage tank. Probe lead 36 is used to insert the probe 15 into the tank 34 and an electric cable 37 connects the probe to a probe cap 38. The tank opening 39 is closed by probe cap 38 (FIG. 5D) which contains electrical circuit means 40 (FIG. 10) which lights LED's 41, 42, and 43 (FIG. 10) in the cap 38 to provide an indication of the fluid environment of the monitoring elements 16, 18 and 19. In the preferred embodiment, the LED's are colored and a green LED indicates the presence of air (the dry condition), a yellow LED indicates the presence of water, and a red LED indicates the presence of hydrocarbon. The electronics also provide signals on outputs 45, 46, and 47 which may be connected to a central monitoring station (not shown) which simultaneously monitors a number of detectors in a number of tanks at remote locations.

Figure 10:
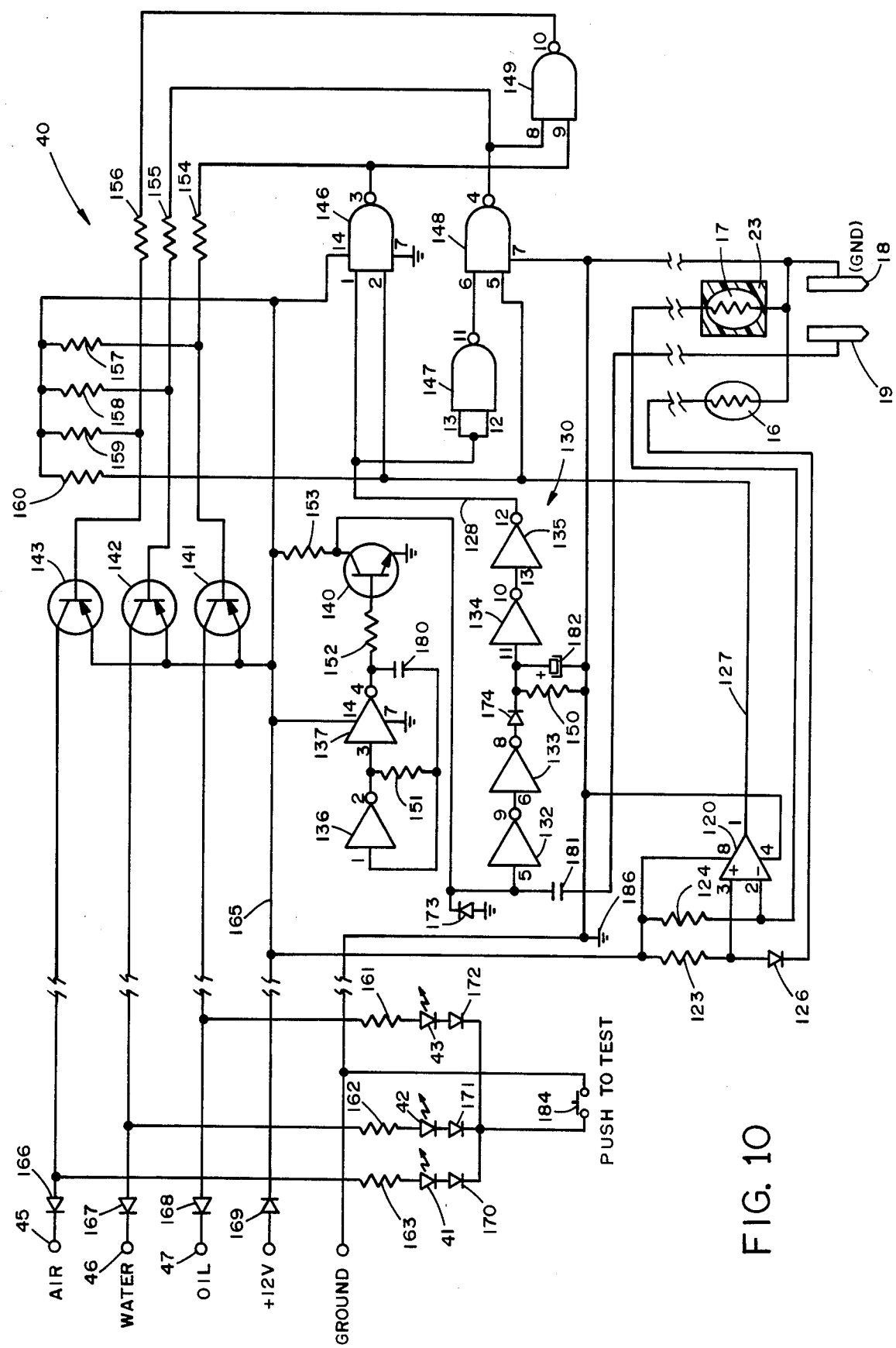
FIG. 10 is an electrical circuit diagram of a detector according to the invention.

Turning now to a more detailed description of the invention, the probe casing 20 is generally in the form of a thin box with rounded ends 50 and 51. It includes a casing body 21 and a cover 24. In the preferred embodiment, casing 20 is about 2½ inches long, 1⅛ inches wide, and ⅜ inches deep. Slots 48 and 49 are formed in ends 50 and 51 respectively. Slot 48 is of a size to receive and hold probe lead 36 and slot 49 is of a size appropriate to receive and hold electric cable 37. Two partitions 53 and 54 form a chamber 28 in casing 20. Openings 26 are formed in casing body 21 and cover 24. Preferably openings 26 are ¼ inches by 1/16 inch and have rounded ends. Slots 56, 57 and 58 are formed in partition 54 to receive the necks of monitoring elements 16, 18 and 19. The slots are of a size that will hold the elements securely. A frame 60 is also formed in casing body 21. A slot 61 is formed in one end 62 of the frame 60 to receive and hold the leads 64 of monitoring element 17. The frame 60 is filled with an insulating material 23 to encapsulate element 17. Casing 20 also includes connector 67, the face of which is shown in FIG. 3. Connector 67 includes conductive traces 68 which form part of electric circuit 40 (FIG. 10). Wires 69 are part of cable 37 and connect to the traces 68. One lead connecting to monitoring element 16 is covered by an insulating sleeve 70 and the other lead 71 runs at an angle to the connector 67.

Connector 67 is the same height as partitions 53 and 54, which height is less than the height of the outer wall 22 of casing body 21 in an amount equal to the thickness of cover 24. The cover 24 is of a size to fit just within the inner periphery of wall 22. Thus the cover 24 when inserted in place is supported by connector 67 and partitions 53 and 54 to provide a flush exterior for casing 20. Collar 72 is attached to cable 37 to absorb any strain exerted on cable 37 that would tend to pull on the connections between wires 70 and traces 68. Lead 36 has a ball 74 attached to one end to prevent it from pulling out of slot 48. The other end has a loop 75 formed in it, which loop is secured by a cable tie 76 having a set screw 77. The length of lead 36 is sufficient to extend it at least half way around the tank 34 and out of tank opening 39 (FIG. 5D).

Figure 5D:
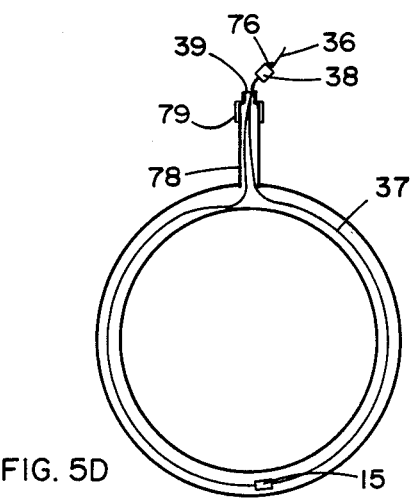
Figure 6:
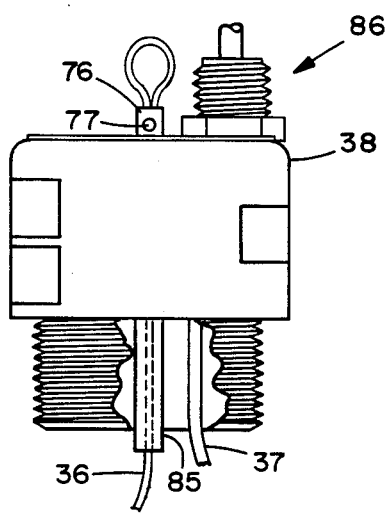
FIG. 6 shows detail of the probe cap and lead.

Turning now to FIGS. 5A through 5D, the preferred method of insertion of the probe 15 into a double-walled tank 34 is shown. Tank 34 is shown sectioned through a fill port 78 which includes a threaded end member 79. The distal end 81 of an electrician's fish 80 is inserted in the tank opening 39 and runs around the tank until end 81 returns to the port 78 (FIG. 5A). A hook 82 or other engaging member is inserted through opening 39 (FIG. 5B), the end 81 is engaged by hooking it, and is then pulled out of the tank opening 39. The loop 75 at the end of the probe lead is attached to the distal end 81 of the fish by means of the conventional snubbing hook 83 at the end of the fish (FIG. 5C) and the probe lead and probe are pulled around the tank until the probe is located in the desired position, which is generally the lowest point in the tank (FIG. 3B). The lead 36 will extend out of the tank opening 39 when the probe 15 is in position. The lead loop 75 is disconnected from the fish end 81, the set screw 77 loosened, the cable tie 76 is removed from the lead 36 and the lead 36 is pulled through the lead guide 85 in the probe cap 38 (FIG. 5D and shown in detail in FIG. 6). Tie 76 is then replaced on the lead wire 36, the cap 38 is installed on the threaded end element 79 of port 78, the slack in the lead is pulled up, and the set screw 77 in tie 76 is tightened down with a wrench. An electric cable connector 86 may be attached to connect the probe electronics 40 (FIG. 10) to a central monitoring station (not shown).

Figure 7:
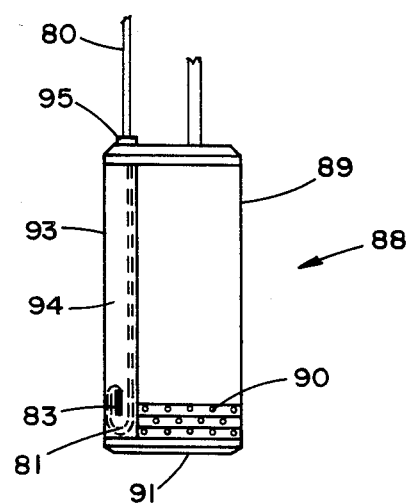
FIG. 7 shows an alternative embodiment of the probe casing.
Figure 8A:
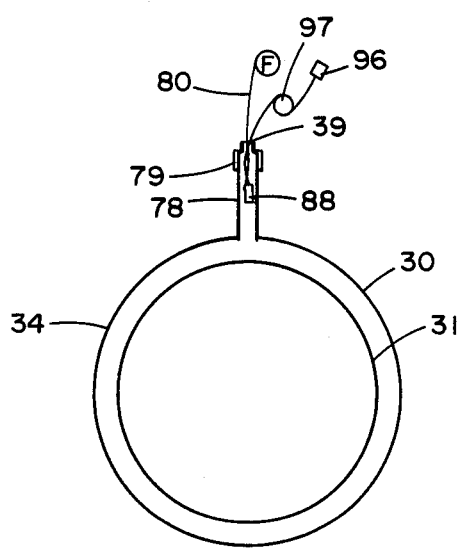
FIGS. 8A through 8C show an alternative method of installing a probe.
Figure 8B:
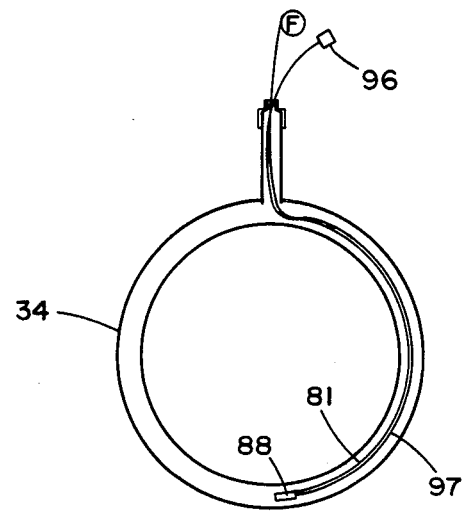
Figure 8C:
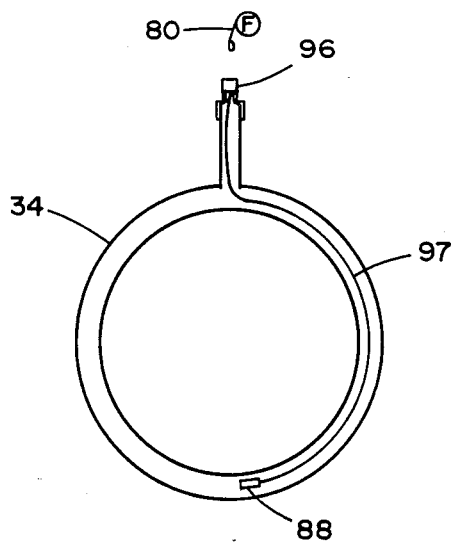

An alternative embodiment of a probe casing 89 according to the invention is shown in FIG. 7. This casing is more rectangular, has smaller openings 90, which are placed near end 91, and includes an extension 93 of the casing which forms a channel 94 for receiving the distal end 81 of fish 80 which is inserted through opening 95. The probe of FIG. 7 may be installed in a tank 34 in an alternative method shown in FIGS. 8A through 8C. The fish distal end 81 is inserted into channel 94 in probe casing 89 (FIG. 8A) an the probe is inserted through tank opening 39 and pushed down port 78 and into position in the tank (FIG. 8B). The fish is then withdrawn from the tank and the tank port 78 is closed with probe cap 96. In this embodiment, the probe cable 97 may be used to withdraw the probe casing 89 from the tank 34.

Figure 9:
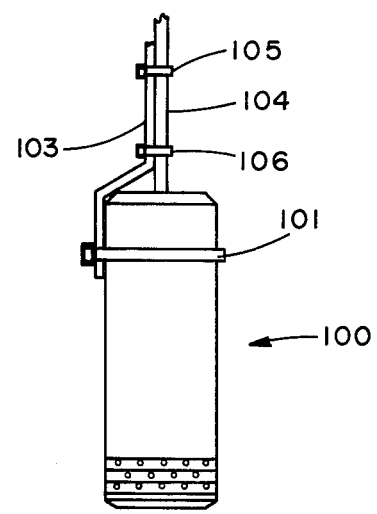
FIG. 9 shows another alternative embodiment of the probe attached to apparatus for another alternative installation method.

Another embodiment of a probe 100 according to the invention is shown in FIG. 9. This embodiment is similar to the embodiment of FIG. 7, except that the casing extension 93 has been eliminated. This embodiment is installed using a stiff rod 103 which is fastened to probe 100 by means of bracket 101 and to the probe cable 104 by clamps 105 and 106. This probe may be inserted into a small area simply by pushing it into place with rod 103.

Turning now to FIG. 10, the preferred detector electronics according to the invention includes monitoring elements 16, 17, 18 and 19, comparator 120, inverters 132 through 137, transistors 140 through 143, NAND gates 146 through 149, resistors 123, 124 and 150 through 163, diodes 127 and 166 through 174, light-emitting diodes (LED's) 41, 42 and 43, capacitors 180, 181, and 182, and switch 184. The ground is indicated as at 186. The numbers on the inputs and outputs of the gates (inverters and NAND gates) such as the 1 on the input to inverter gate 136, indicate the pin number of the IC's these devices are part of (see below).

The circuit composed of inverters 136 and 137, resistor 151, and capacitor 180 is an approximately 670 Hertz oscillator. The output of inverter 137 is applied to its input through capacitor 180 and resistor 151. The line between capacitor 180 and resistor 151 is also connected to the input of inverter 136. The output of inverter 136 is connected to the input of inverter 137. The No. 14 pin of the inverter 137 is connected to the 12 volt power line 165, while the No. 7 pin is connected to ground. The output of inverter 137 is also connected to the base of transistor 140 through resistor 152. The emitter of transistor 140 is connected to the ground. The collector is connected to the +12 V power supply line 165 through resistor 153.

The collector of transistor 140 is also connected to ground through diode 173, with the anode of diode toward the ground, to monitoring element 19 through capacitor 181, and to the input of inverter gate 132. The output of inverter 132 is connected to the input of inverter 133 and the output of inverter 133 is connected to the anode of diode 174. The cathode of diode 174 is connected to the input of inverter 134 and to monitoring element 18 through resistor 150 and capacitor 182 in parallel. Monitoring element 18 is also connected to ground. The output of inverter 134 is connected to the input of inverter 135 and the output of inverter 135 is connected to one input of NAND gate 146 and both inputs of NAND gate 147.

The non-inverting (+) input (pin #3) of comparator 120 is connected to monitoring element 16 through diode 126, with the anode of the diode toward the input, and is also connected to the +12 V power line 165 through resistor 123. The inverting (−) input (pin #2) of comparator 120 is connected to monitoring element 17 and also to the +12 V power line 165 through resistor 124. The number 8 pin of comparator 120 is connected to the 12 V power line 165 while its number 4 pin is connected to ground. The output of comparator 120 (pin #1) is connected to the other input of NAND gate 146, to one input of NAND gate 148, and to the +12 V power line 165 through resistor 160.

The output of NAND gate 147 is connected to the other input of gate 148. The output of NAND gate 146 is connected to one input of NAND gate 149 and to the base of transistor 141 through resistor 154. The output of NAND gate 148 is connected to the other input to NAND gate 149 and to the base of transistor 142 through resistor 155. The output of NAND gate 149 is connected to the base of transistor 143 through resistor 156. The bases of transistors 141, 142 and 143 are also each connected to the power line 165 through resistors 157, 158 and 195, respectively.

The emitters of transistors 141, 142 and 143 are connected to the power line 165. The collectors of each of transistors 141, 142 and 143 are connected to the anodes of LED's 43, 42 and 41, respectively through resistors 161, 162 and 163, respectively. The cathode of each of LED's 41, 42 and 43 are connected to the anodes of diodes 170, 171 and 172, respectively. The cathode of diodes 170, 171 and 172 are each connected to one side of switch 184. The other side of switch 184 is connected to ground. The collector of transistors 143, 142 and 141 are also connected to the "AIR", "WATER" and "OIL" outputs 45, 46, and 47 respectively through diodes 166, 167 and 168, respectively with the anodes of the diodes toward the transistors. The "AIR", "WATER" and "OIL" outputs connect to a central station (not shown) which monitors the outputs of many detector-probe assemblies, such as the one just described, at different remote locations. The power line 165 is connected to the +12 V power input through diode 169 with the anode of the diode toward the input. The +12 V power input and the ground are connected to the respective outputs of the power supply of the central station.

In the preferred embodiment, casing 20 is molded out of PVC, the connector 67 is an etched circuit board with copper traces, the probe lead 36 is a nylon coated stainless-steel cable about 1/16 inches in diameter, the electric cable 37 is a teflon insulated electric cable, the fish 80 is a ¼ inch electrician's fish, monitoring elements 16 and 17 are Fenwall GB32P2 thermistors, monitoring elements 18 and 19 are 20 gauge stainless steel wire, insulating material 23 is GE-118 self-leveling RTV (Room Temperature Vulcanizer), probe cap 38 is made of PVC, and lead tie 85, bracket 101, rod 103 and clamps 105 and 106 are made of stainless steel.

The preferred electronic circuit parts (FIG. 10) are as follows: inverters 132 through 137 are a six-inverter package type 4069, transistor 140 is a PN2222, transistors 141 through 143 are PN2907's, comparator 120 is a type LM2904, gates 46 through 49 are a four-gate IC package type 4011, resistors 150, 151, 152 and 153 are 100K ohm, 220K ohm, 100K ohm, and 150K ohm, respectively, resistors 123 and 124 are each 560 B.L.C. ohm, resistors 154, 155 and 156 are each 10K ohm, resistors 157 through 160 are 100K ohm, and resistors 161, 162 and 163 are 820 ohm, capacitor 180 is a 0.0047 microfarad, 181 is a 0.1 microfarad capacitor, and 182 is a 1 microfarad capacitor, diodes 126, 166 through 169, and 173 are IN4001's, and 170, 171, and 172 and 174 are IN914's. LED's 41 through 43 are green, yellow, and red LED's respectively.

The invention operates in the following manner. Fluids between the walls of tank 34 enter chamber 28 and contact monitoring elements 16, 18 and 19. Thermistors 16 and 17 along with resistors 123 and 124 and diode 126 form a resistance bridge. Comparator 120 and its associated circuitry comprise a fluid-state (gas or liquid state) detector. The value of the resistors 123 and 124 are sufficiently low so that the current through the thermistors 16 and 17 will be sufficient to self-heat them and cause their resistance to lower from their ambient temperature value. Diode 126 provides some voltage compensation for the circuit of thermistor 17 to adjust for the fact that the RTV cools thermistor 17 below the temperature of thermistor 16 in air. In this (dry) condition, thermistor 16 heats itself and lowers its resistance below that of thermistor 17. The voltage at pin #3 of comparator will be lower than pin #2 and its output will be low. This low signal on line 127 is applied to one input of NAND gates 146 and 148 which causes their output to be high which disables the "Water" and "Oil" outputs 46 and 47. At the same time, a high signal is put on inputs 8 and 9 of NAND gate 149 which causes its output to go low, turning on transistor 143 to provide a high signal on the "AIR" output and causing the green LED 41 to light when switch 184 is closed. When the probe 15 is submerged in a liquid (water or hydrocarbon) thermistor 16 cools more rapidly than thermistor 17 which causes its resistance to increase which causes the voltage at pin 3 of comparator 120 to rise above the voltage at pin 2. The output of comparator 120 (line 127) will go high, which high is applied to pins 2 and 5 of the NAND gates 146 and 148 respectively which permits the outputs of these gates to be determined their other inputs (pins 1 and 6) which are controlled by the polar-non-polar detector means 130 comprising inverters 132 through 135 and their associated circuitry. The polar-non-polar detector signal (on line 128) is generated in the following manner. The inverters 136 and 137 and their associated circuitry comprise a 670 Hertz oscillator which provides an oscillating signal at the output (pin 4) of inverter 137. Transistor 140 isolates the oscillator from the rest of the circuitry and inverts the oscillating signal. The signal is passed to monitoring element 19 through isolation capacitor 181. Diode 173 passes any negative going current induced on the element 19 to ground. Gate 132 requires from about 4 to 9 volts to trigger its output from a high to low state; this prevents positive going induced current from affecting the detector output. If the elements 18 and 19 are in a non-polar fluid, such as air or hydrocarbon, on the high part of the oscillation inverter 132 goes low, inverter 133 goes high, inverter 134 goes low, and inverter 135 goes high to produce a high signal on line 128. The capacitor 182 will discharge the high signal at the input to inverter 134 if the high in the output of inverter 133 is not refreshed. So long as the probes are in a non-polar fluid, the high is refreshed about 670 times a second. Resistor 150 determines the time constant for discharge of capacitor 182. Diode 174 prevents the capacitor 182 from discharging to the low on the output of inverter 133 during the low part of the oscillation. If the elements 18 and 19 are immersed in a polar fluid, such as ground water, there is essentially a short across the elements and the ground of element 18 pulls element 19 and the input of inverter 132 low, which produces a low signal on line 128.

The gates 146 through 149 provide a logic network responsive to the fluid state characteristic signal on line 127 and the fluid polar characteristic signal on line 128 to provide an indication of whether the fluid environment of the monitoring elements 16, 18, 19 is a gas or a polar or non-polar liquid. As discussed above, when the fluid state signal on line 127 is low the outputs indicate "AIR". In a similar manner the other combinations of data input signals will produce a high signal on the "WATER" output 46 when the monitoring elements are in water and a high signal at the "OIL" output 47 when the monitoring elements are in hydrocarbon, and when switch 184 is closed light LED's 42 and 43 respectively. Diodes 166 through 169 provide reverse bias protection and resistors 154 through 156 limit the current. Resistors 157 through 160 are pull up resistors. Likewise diodes 70, 71 and 72 provides isolation protection and resistors 161, 162 and 163 provide the current-limiting effect for their respective LED's.

The encapsulating of monitoring element 17 in an insulator is an important feature of the invention. The insulator should be chosen to have a thermal conductivity greater than that of air but preferably within about 0.5 BTU/$(ft)$ (°F./hr) of air. The preferred RTV has a thermal conductivity of about 0.11 BTU/ft (°F./hr) which is about 10 times that of air. The above relationship of the thermal conductivities of the insulator and air provides the proper sign of the voltage at pins 2 and 3 of comparator 120 for all the operating environments.

As a result of the potting of the reference thermistor in an insulator as described above, the electrical circuitry can be made very simple and packaged in a small space. At the same time, the insulator protects the reference thermistor from contamination from the environment and allows it to be located close to the detecting thermistor 16, both of which are important for reliable operation.

A novel apparatus for detecting fluids which is simple, small and reliable has been described. Although the invention has been described in terms of specific embodiments, this is not intended to limit the invention. It is evident that those skilled in the art may now make many uses and modifications of the embodiments described, without departing from the inventive concepts. For example, other equivalent electronic parts may be used, or other encapsulating insulations may be used. Consequently, the invention is to be construed as embracing each and every novel feature and novel combination of features present in the detector described.

What is claimed is:

1. Apparatus for detecting the presence of fluids comprising:
    a first monitoring element having a surface exposed for contact with the fluids to be monitored;
    a second monitoring element having a surface encapsulated in a thermal insulator;
    each of said monitoring elements having an electrical characteristic that changes with temperature; and
    electrical circuit means for heating said monitoring elements, said circuit including output means responsive to changes in said characteristic to provide an indication of the fluid environment of said elements.

2. The apparatus of claim 1 wherein said thermal insulator conducts heat better than air.

3. The apparatus of claim 2 wherein said thermal insulator is RTV (Room Temperature Vulcanizer).

4. The apparatus of claim 1 and further comprising third and fourth monitoring means for providing an oscillating voltage to said third and fourth monitoring elements and polar-non-polar fluid detector means for providing a fluid polar characteristic signal, and wherein said output means includes fluid state detector means for providing a fluid state characteristic signal and logic means responsive to said fluid polar characteristic signal and said fluid state characteristic signal for providing a indication of whether said fluid is a gas or a polar or non-polar liquid.

5. The apparatus of claim 4 wherein said gas is air, said polar liquid is water and said non-polar liquid is a hydrocarbon.

6. The apparatus of claim 1 wherein said output means includes a voltage comparator having a first input electrically connected to said first monitoring element and a second input electrically connected to said second monitoring element.

7. The application of claim 6 wherein said changeable electrical characteristic is resistance and further including resistance bridge connecting said monitoring elements, said bridge having resistance values such that when said monitoring elements are in air the voltage at said first input s lower than the voltage at said second input and when said monitoring elements are in liquid the voltage at said first input is higher than the voltage at said second input.

* * * * *